(12) United States Patent
Bothe et al.

(10) Patent No.: US 11,331,469 B2
(45) Date of Patent: May 17, 2022

(54) IMPLANTABLE FLUID PUMP SYSTEM

(71) Applicant: Albert-Ludwigs-Universität Freiburg, Freiburg (DE)

(72) Inventors: Wolfgang Bothe, Freiburg (DE); Christoph Benk, Freiburg (DE); Koppany Sarai, Wasenweiler (DE); Friedhelm Beyersdorf, Freiburg (DE)

(73) Assignee: ALBERT-LUDWIGS-UNIVERSITÄT FREIBURG, Freiburg (DE)

( * ) Notice: Subject to any disclaimer, the term of this patent is extended or adjusted under 35 U.S.C. 154(b) by 222 days.

(21) Appl. No.: 15/779,362

(22) PCT Filed: Nov. 24, 2016

(86) PCT No.: PCT/EP2016/078630
§ 371 (c)(1),
(2) Date: May 25, 2018

(87) PCT Pub. No.: WO2017/089440
PCT Pub. Date: Jun. 1, 2017

(65) Prior Publication Data
US 2018/0303987 A1 Oct. 25, 2018

(30) Foreign Application Priority Data
Nov. 27, 2015 (DE) ...................... 10 2015 223 541.6

(51) Int. Cl.
*A61M 60/857* (2021.01)
*A61M 60/148* (2021.01)
*A61M 39/10* (2006.01)

(52) U.S. Cl.
CPC .......... *A61M 60/857* (2021.01); *A61M 39/10* (2013.01); *A61M 60/148* (2021.01); *A61M 2039/1038* (2013.01)

(58) Field of Classification Search
CPC ........................... A61M 1/122; A61M 1/1008
(Continued)

(56) References Cited

U.S. PATENT DOCUMENTS 4,955,856 A * 9/1990 Phillips .................... A61M 1/10
600/16
5,167,623 A * 12/1992 Cianci ............... A61M 25/0026
604/43
(Continued)

FOREIGN PATENT DOCUMENTS

WO 2007/067792 A2 6/2007
WO 2007/103464 A2 9/2007
(Continued)

OTHER PUBLICATIONS

International Search Report for PCT/EP2016/078630 mailed Jan. 26, 2017; English translation submitted herewith 7 pages).

*Primary Examiner* — John R Downey
(74) *Attorney, Agent, or Firm* — Fitch, Even, Tabin & Flannery LLP

(57) ABSTRACT

An implantable fluid pump system is disclosed for supporting or initiating flow inside a hollow organ through which fluid circulates, in particular the heart. The fluid pump system comprises an intracardiac module, which includes two separate fluid channels, each of which possesses an intracardiac fluid channel opening and, located opposite the latter, an extracardiac fluid channel opening, a fastening module, which provides a joining contour for purposes of joining onto the intracardiac module in a fluid-tight manner, and a fastening structure for purposes of intracorporeal fastening onto the hollow organ, and a pump module, which can be mounted in a releasable manner directly or indirectly onto the intracardiac module, and can be attached in a fluid-tight manner to the extracardiac fluid channel openings (Continued)

in order to produce a fluid-tight connection of both fluid channels.

18 Claims, 12 Drawing Sheets

(58) Field of Classification Search
  USPC .............................................. 600/16
  See application file for complete search history.

(56) References Cited

U.S. PATENT DOCUMENTS

| | | | | |
|---|---|---|---|---|
| 6,059,760 | A * | 5/2000 | Sandmore | A61M 25/007 604/264 |
| 6,949,065 | B2 * | 9/2005 | Sporer | A61M 1/1049 600/16 |
| 7,217,236 | B2 * | 5/2007 | Calderon | A61M 1/1098 600/16 |
| 8,231,519 | B2 * | 7/2012 | Reichenbach | A61M 1/3653 600/16 |
| 8,852,072 | B2 | 10/2014 | Larose et al. | |
| 8,870,739 | B2 * | 10/2014 | La | A61M 1/12 600/16 |
| 2001/0041934 | A1 | 11/2001 | Yamazaki et al. | |
| 2004/0002624 | A1 * | 1/2004 | Yu | A61M 1/3659 600/16 |
| 2007/0134993 | A1 * | 6/2007 | Tamez | A61M 1/1008 439/752 |
| 2009/0203957 | A1 * | 8/2009 | La | A61M 1/122 600/18 |
| 2009/0264697 | A1 * | 10/2009 | Tovar Lopez | A61M 1/106 600/16 |
| 2010/0249489 | A1 | 9/2010 | Jarvik | |
| 2010/0298625 | A1 * | 11/2010 | Reichenbach | A61M 1/3653 600/16 |
| 2011/0238172 | A1 * | 9/2011 | Akdis | F04D 13/0666 623/3.11 |
| 2011/0298304 | A1 * | 12/2011 | Cotter | H01R 13/5224 307/147 |
| 2012/0059212 | A1 * | 3/2012 | LaRose | A61M 1/12 600/16 |
| 2013/0133944 | A1 | 5/2013 | Teraura et al. | |
| 2014/0364880 | A1 | 12/2014 | Farnan et al. | |
| 2015/0104331 | A1 * | 4/2015 | Dye | A61M 1/1008 417/53 |
| 2017/0157309 | A1 * | 6/2017 | Begg | F04D 29/242 |

FOREIGN PATENT DOCUMENTS

| | | |
|---|---|---|
| WO | 2012/165429 A1 | 12/2012 |
| WO | 2014/145667 A2 | 9/2014 |
| WO | 2016/077444 A1 | 5/2016 |
| WO | 2016/100600 A2 | 6/2016 |

* cited by examiner

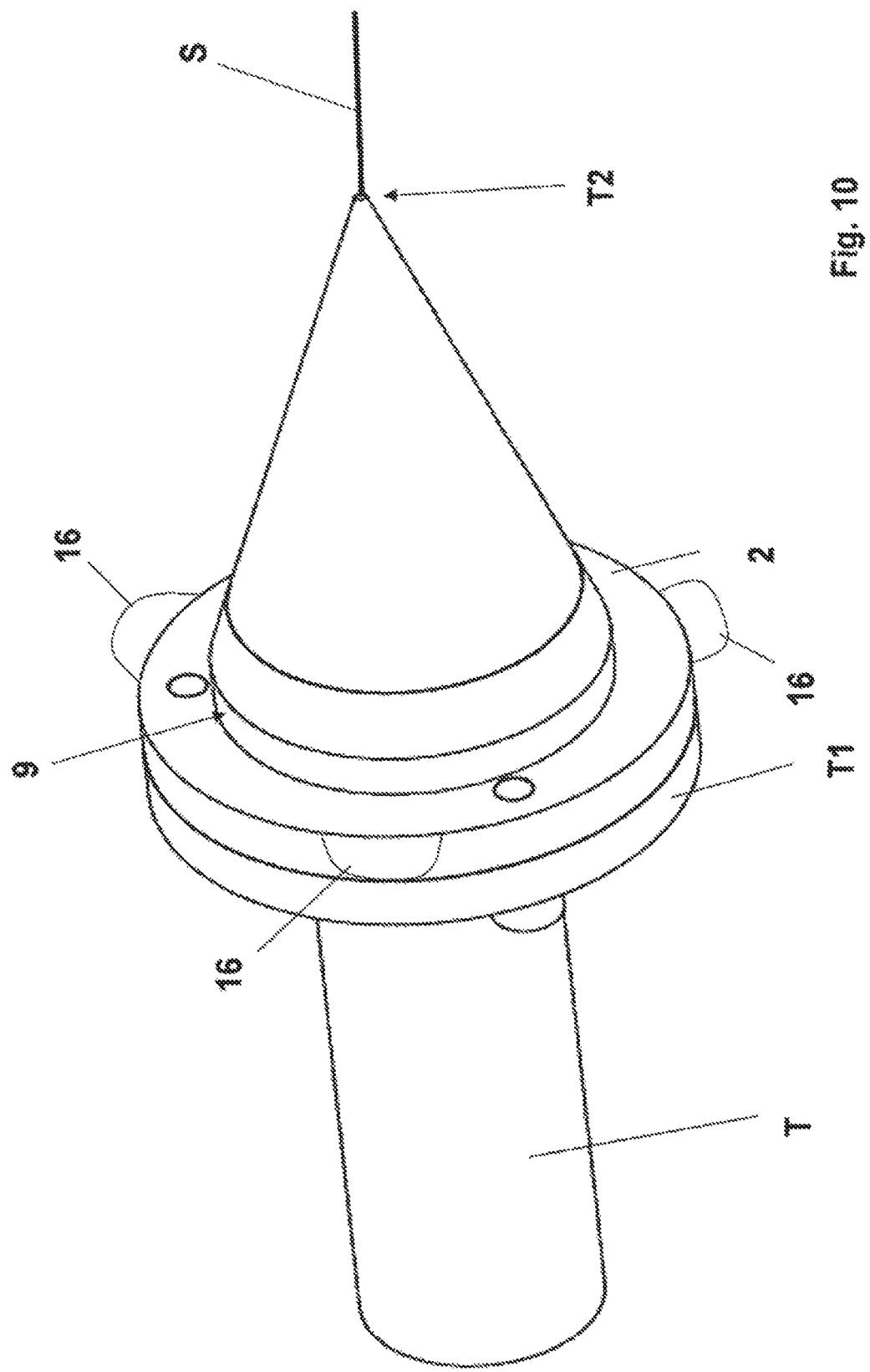

IMPLANTABLE FLUID PUMP SYSTEM

CROSS REFERENCE TO RELATED APPLICATIONS

Reference is made to PCT/EP2016/078630 filed Nov. 24, 2016, and German Application No. 10 2015 223 541.6 filed Nov. 27, 2015, which are incorporated herein by reference in their entirety.

BACKGROUND OF THE INVENTION

Field of the Invention

The invention relates to an implantable fluid pump system for supporting or initiating flow inside a hollow organ through which fluid circulates, in particular the heart.

Description of the Prior Art

Implantable fluid pump systems of the type cited above serve primarily as cardiac support systems, which in English are referred to as VADs (Ventricular Assist Devices). Such implantable fluid pumping systems, serving to provide cardiac support, are implanted in the left, right, or both chambers of the heart in cases of severe cardiac disease, as a result of which the blood supply to the body is adequately guaranteed. In most cases such systems, also referred to as artificial heart fluid pumping systems, are implanted to cover the time until a heart transplant. In the case of left ventricular failure, the fluid pumping system is implanted into the left ventricle, wherein the pumping system is connected to the aorta via an appropriate intracardially laid tubus to deliver blood from the left ventricle to the aorta in a pulsating or continuous manner, depending on the pumping mechanism employed.

Modern, miniaturized, intracardiac fluid pumping systems allow an intracardiac implantation using minimally invasive surgical techniques. In this way, complex surgical interventions, such as anastomosis of the ventricular myocardium and aorta, and the use of a heart-lung machine, can be avoided.

US Published Application 2010/0249489 A1 discloses a modern intracardiac fluid pumping system that can be intracardially implanted using the Seldinger technique via the apex of the heart, with an anchorage in the region of the heart valves, without the use of a heart-lung machine and without anastomosis of the aorta. The intraventricular blood pumping system of known art has a motor-driven fluid pump with an axial fluid flow, which is inserted within a tubus. The tubus has an open end within the ventricular lumen, through which blood is sucked. The end of the tubus that is axially opposite to the open end is connected in a fluid-tight manner to a tubular extension, which leads through the region of the heart valves and opens out into the aorta. For purposes of intracardiac attachment of the tubular extension together with the tubus, a dilatation element replacing the heart valve function is mounted in the region of the tubular extension which ensures a secure seating for the intracardiac fluid pumping arrangement. An electrical lead serves to supply electrical power and enables activation of the electromotively driven fluid pump. The electrical lead runs extracardially through an implantation-related lesion introduced apically into the myocardium. The lesion is sealed in a fluid-tight manner with a surgical thread.

An alternative ventricular support system is disclosed in U.S. Pat. No. 8,852,072, which comprises an axial fluid pump fully introduced into the ventricle, on the discharge side on which a tubular extension is mounted, which leads through the region of the heart valves and opens out into the aorta. For purposes of intracardiac attachment and in particular an intracardiac arrangement in which the pump suction tract is spaced apart from the endocardium. The entire intracardiac fluid pumping system is supported by a rod-shaped spacer on a support plate that is surgically attached to the myocardium and also seals in a fluid-tight manner the implantation-related apical lesion in the myocardium. In order to achieve an intracardiac mobility, so as not to impair the dynamics of the heart muscle movement at all, or as little as possible, the rod-shaped spacer is connected to the myocardial fixed support plate via a ball joint.

An artificial cardiac support system in which the pump is arranged inside the cardiac lumen is disclosed in US published application 2001/0041934 A1. Here the pumping system which is of known art is securely anchored to the housing, so that a selective pump replacement is not possible for technical reasons.

US published application 2014/0364880 A1 discloses a conventional blood pump, with which blood from one chamber is re-introduced extracardially and with the aid of a pump, via a long stent, into another chamber. The fastening arrangement for the pumping system on the heart muscle is a commercial design.

Document WO 2014/145 667 A2 discloses a blood pumping system in the evacuative aorta.

US published application 2013/0133 944 A1 discloses a pumping system with an extracavitary mount of the motor and pump. In extracorporeal heart support systems three tubes are fed out of the body as a blood supply, a blood drain, and a power cable. All the tubes are led out of the body from one single access to minimize the surgical burden on the patient.

The document WO 2007/103 464 A2 describes a pumping system with an extracavitary mounting of motor and pump. Essentially this is a blood pump that is primarily used as a dialysis pump.

Although the minimally invasive implantable intraventricular blood pump systems of known art can be implanted in a patient-friendly surgical technique, any subsequent manipulations of the fully intracardially introduced ventricular support systems can be undertaken only by way of a complete explantation. In addition to the minimally invasive intervention that is basically stressful for the patient, the heart valves that come into contact with at least one of the intravascular support system and the vessel wall sections adjoining the heart valves experience in particular a considerable, sometimes irreversible, irritation which, in principle, must be minimized or avoided altogether.

SUMMARY OF THE INVENTION

The invention is an implantable fluid pumping system for supporting or initiating flow inside a hollow organ through which fluid circulates, in particular the heart, such that on the one hand, as in the above-described intravascular support systems of known art, a minimally invasive and thus patient-friendly implantation technique can be applied without the need for a heart-lung machine while on the other hand, however, the possibility exists of explanting at least individual components, in particular the motor-driven fluid pump in the event of a required replacement, without thereby dislocating intracardially implanted components of the fluid pumping system, and thus irritating heart valves or heart valve regions or similar intracardiac regions.

The inventive implantable fluid pumping system, which can be used for supporting or initiating flow inside an intracorporeal hollow organ of a human or an animal through which fluid circulates, but is particularly suitable for minimally invasive implantation in a human heart, is basically a modular structure, which allows the minimally invasive implantation procedure to be executed in a manner that is extremely benign for the patient. The individual components are gradually implanted on or into the hollow organ and are assembled intracorporeally in a modular manner. In this way, all intracorporeal regions of tissue affected by the implantation procedure are maximally protected, that is, minimally irritated. Similarly, the modular design allows access to the electromotively driven pump, in the event of a required replacement, in the case of an already implanted fluid pumping system, without the need to open locally in a minimally invasive manner the respectively affected hollow organ; in the case of the heart this especially concerns the myocardium. For this purpose, the implantable fluid pumping system designed in accordance with the invention is supported directly on the peripheral edge of a minimally invasive opening introduced into the wall of the hollow organ, which opening, at the same time, is sealed in a fluid-tight manner by the fluid pumping system extending through the opening. Thus, the implantable fluid pumping system designed in accordance with the invention has component parts that are arranged intravascularly, together with other component parts that are arranged and accessible extravascularly.

The implantable fluid pumping system disclosed below for purposes of supporting or initiating flow inside a hollow organ through which fluid circulates is particularly suitable as a cardiac support system. The further description thus relates predominantly to the case of the implantation of a fluid pumping system in or on the heart, although an application of the system on or in other hollow organs through which blood or lymph circulates is also possible. In the case of non-cardiac implantation, the terms "intracardiac" and "extracardiac" used in the context of a heart should be replaced by "intravascular" and "extravascular".

The inventive implantable fluid pump system has at least one intracardiac module (or intravascular module), a fastening module, together with a pump module.

The intracardiac module comprises two separate fluid channels, each possessing an intracardiac and an extracardiac fluid channel opening. The term "intracardiac" is intended here to characterize that the fluid channel opening of the respective fluid channels, which in the implanted state of the fluid pump system is arranged within the heart, that is to say, within a heart chamber. Whereas the term "extracardiac" characterizes that fluid channel opening, which, owing to the physical design and arrangement of the intracardiac module in the implanted state is arranged outside the heart, or at least in a direction in which the opening faces away from the heart.

The fastening module serves the purpose of supporting and attaching the entire fluid pumping system on the heart or within the heart. The fastening module has a joining contour, via which the intracardiac module can be joined with the fastening module in a fluid-tight manner. In addition, the fastening module provides a fastening structure for intracorporeal fastening to the heart. In a preferred embodiment, the fastening module is basically designed in the form of an annulus or tubus, with a radially inwards oriented outer surface, which corresponds to the above-identified joining contour for purposes of joining to the intracardiac module in a fluid-tight manner. In the radially outwards direction, the fastening module likewise provides a suitably designed joining contour, against which, in the implanted state of the inventive fluid pump system, the myocardial wall of an apical local lesion in the myocardium fits peripherally, completely surrounding the contour. The joining contour is preferably designed at least partially in the form of a straight cylinder. Alternatively, joining contours deviating from the cylindrical shape are also conceivable, for example conical, prismatic, that is to say, n-sided, etc. The fastening module can be attached to the myocardium using a suitably selected surgical fastening technique, for example, with the aid of a surgical thread or surgical clamps. Further details can be found in conjunction with the description of a specific embodiment.

A preferred modification of the fastening module provides a reduced pressure which is a suction-assisted temporary attachment of the fastening module to the myocardial outer wall, allowing the surgeon accurately to position the fastening module and, if necessary, to re-adjust the latter, without any damage to the myocardial wall. After correct mounting of the fastening module onto the myocardium, a permanent attachment of the module is made using adhesive technology. For this purpose, the fastening module provides a plurality of groove-like recesses facing towards the myocardial wall. For purposes of temporarily adhering the fastening module to the myocardial wall, a reduced pressure is applied along at least one selected recess. In the state of suction-assisted adhesion, a biocompatible adhesive that is capable of permanently fixing the fastening module to the myocardium is then injected along at least one other groove-shaped recess facing towards the myocardial wall. Furthermore, the adhesive connection creates an airtight joint between the fastening module and the myocardial wall, which can exclude air embolisms.

In the joined state, the fastening module encloses the intracardiac module along the joining contours of respectively matching design. The joining contour of the intracardiac module is located in a medial section of the intracardiac module, which in an axial sequence has extracardiac, medial and intracardiac section. The individual axial sections of the intracardiac module are simply characterized by positioning relative to the heart in the implanted state and in other respects are preferably integrally connected to each other and are preferably made of a uniform material.

In a preferred embodiment, the intracardiac section of the intracardiac module, which, in the implanted state, is within a heart chamber, has both a tubular extension with an open distal tube end that surrounds one of the two fluid channels, and also, is laterally spaced from the tubular extension of the intracardiac fluid channel opening of the other fluid channel.

In another embodiment, the other fluid channel is at least partially designed as an annular channel and is arranged coaxially around the tubular extension, which, as in the preceding embodiment, encloses one of the two fluid channels. In both cases, the two fluid channels are, separately led out from one another, in each case opposite the intracardiac fluid channel openings, into the region of the extracardiac section of the intracardiac module, which in the implanted state is arranged outside the heart and thus is freely accessible extracardially.

The pump module, which can be attached in a fluid-tight manner to the extracardiac fluid channel openings in order to produce a fluid-tight connection between the two fluid channels, in this way can be directly or indirectly fixed securely in a releasable manner onto the extracardiac section of the intracardiac module.

In a preferred embodiment, the pump module has a U-shaped piping system, along which a motor-driven fluid feed pump is introduced. Advantageously, the U-shaped piping system has two open-ended pipe stubs, which can be connected in a fluid-tight and are releasable manner by a fluid-tight plug-in connection with the extracardiac fluid channel openings of the fluid channels surrounded by the intracardiac module. For purposes of electrical power supply as well as for purposes of pump control, the pump module is preferably connected to a cable feed and return, which by virtue of the extracardiac mounting of the pump module also runs outside the heart and thus does not penetrate the myocardium. However, the latter is disadvantageously the case for generic devices of known art.

If, after many years of use of the implanted fluid pumping system, a pump defect or a similar technical malfunction occurs, it is possible to service or replace the pump module without irritating the heart itself with the aid of a minimally invasive intervention.

For purposes of explaining two preferred embodiments of a fluid pump system comprising all components reference will be made below to the descriptions of the Figs.

BRIEF DESCRIPTION OF THE DRAWINGS

The invention will be described below in an exemplary manner by way of embodiments with reference to the Figs., without any limitation of the general inventive concept. Here:

FIG. 10 shows an illustration of a surgical tool for introducing a local lesion within the myocardium for purposes of implantation of the fluid pumping system.

DETAILED DESCRIPTION OF THE INVENTION

Figure 1:
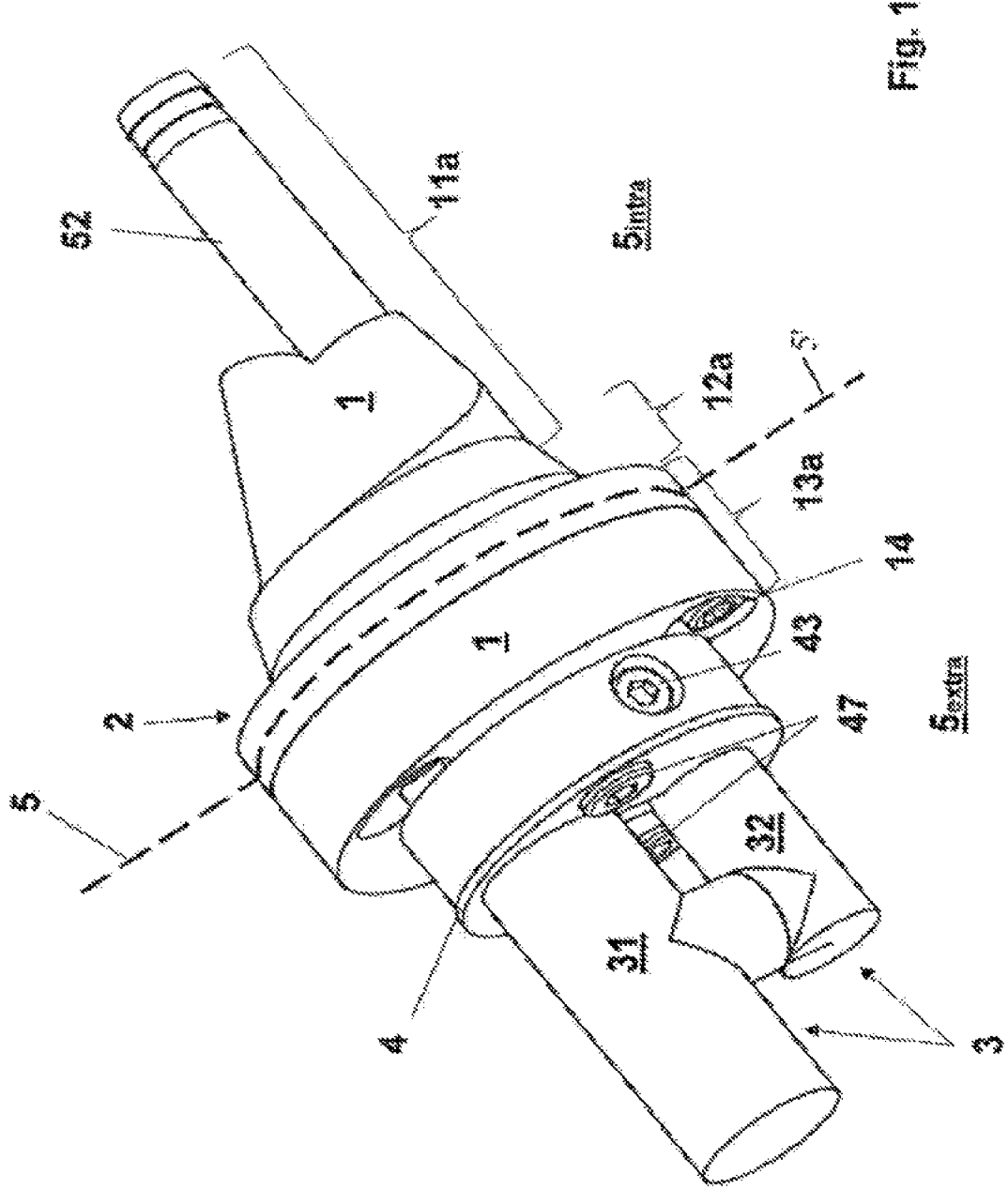
FIG. 1 shows a schematized overall view of a first implantable fluid pump system.

FIG. 1 shows a schematic view in perspective of an embodiment of an implantable fluid pumping system that can be implanted apically into the myocardium of a heart in a minimally invasive manner for purposes of cardiac function support. The fluid pumping system is modular in construction and shows the following individual modules: intracardiac module 1, fastening module 2, pump module 3 and retaining module 4.

All modules can be manipulated individually, that is as individual components, for purposes of both implantation and explantation. The individual components are assembled simply by fitting them together, that is to say, by inserting them into one another, wherein easily accessible screwed joints can be used by a surgeon for purposes of attaching together two components that are in direct contact with one another.

The fluid pumping system supporting the heart function, illustrated in FIG. 1, in addition to its modular structure is characterized in particular by the fact that all components of the fluid pumping system, which otherwise need not come into contact with the heart, are mounted or fixed relative to the heart by way of the fastening module 2. In addition, the fastening module 2 ensures a fluid-tight seal of the implantation-related opening within the myocardium. This is illustrated in a highly schematized manner in the image of FIG. 1 by the dot-dash line having ends 5 and 5' which separates the intracardiac region $5_{intra}$ from the extracardiac region $5_{extra}$. Thus, the fluid pumping system has component parts that in the implanted state have an intracardiac location, in particular these include the intracardiac section 11a of the intracardiac module 1, and component parts that are arranged outside the heart, in particular the latter include the extracardiac section 13a of the intracardiac module 1, the pump module 3 and a retaining module 4 that fixes the pump module 3 to the extracardiac section 13a of the intracardiac module 1 in a fluid-tight manner.

For an explanation of the individual modules, reference is made in the following to the individual images in the later Figs.-.

Figure 2:
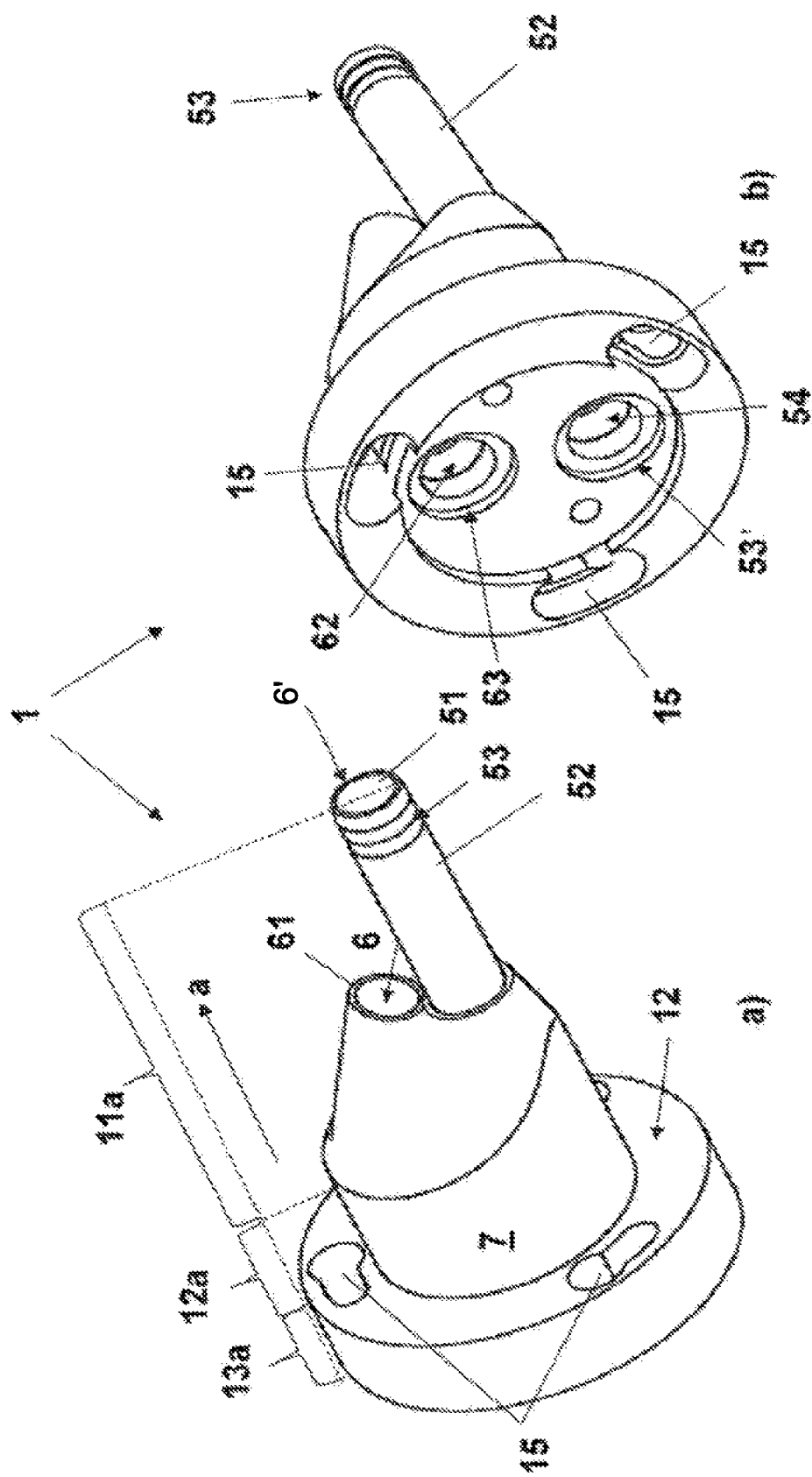
FIGS. 2a and b show illustrations in perspective of a first intracardiac module.

FIGS. 2a, b show in different perspective views the intracardiac module 1 in isolation, which, as already mentioned above, has in an axial direction, along a spatial direction a, an extracardiac section 13a, a medial section 12a immediately adjoining the latter, and an intracardiac section 11a. The intracardiac module 1 is preferably integrally made from a biocompatible material, like the fastening module 2 and the retaining module 4. The intracardiac module 1 essentially comprises two fluid channels 6 and 6', each having open intracardiac fluid channel openings 51 and 61. The first fluid channel 6' has a tubular extension 52 whose length is selected as a function of anatomical proportions. In a preferred embodiment, the tubular extension 52 has a length that is selected such that in the implanted state of the fluid pump system, the fluid channel opening 51 opens out into the region of the aorta. Alternatively, it is possible to select the length of the tubular extension 52 to be appropriately short. By way of a fluid-tight connecting structure 53, which is provided in the region of the fluid channel opening 51. An artificial connecting tubus, which is not shown in FIG. 2, can be securely mounted in a fluid-tight and in a releasable manner onto the tubular extension 52 to guarantee a direct supply of blood to the aorta. The formation of the connecting structure 53 is particularly advantageous in those cases in which the artificial connecting tubus is preferably fixed in the region of the heart valves, for example with the aid of a dilatation element.

Figure 5:
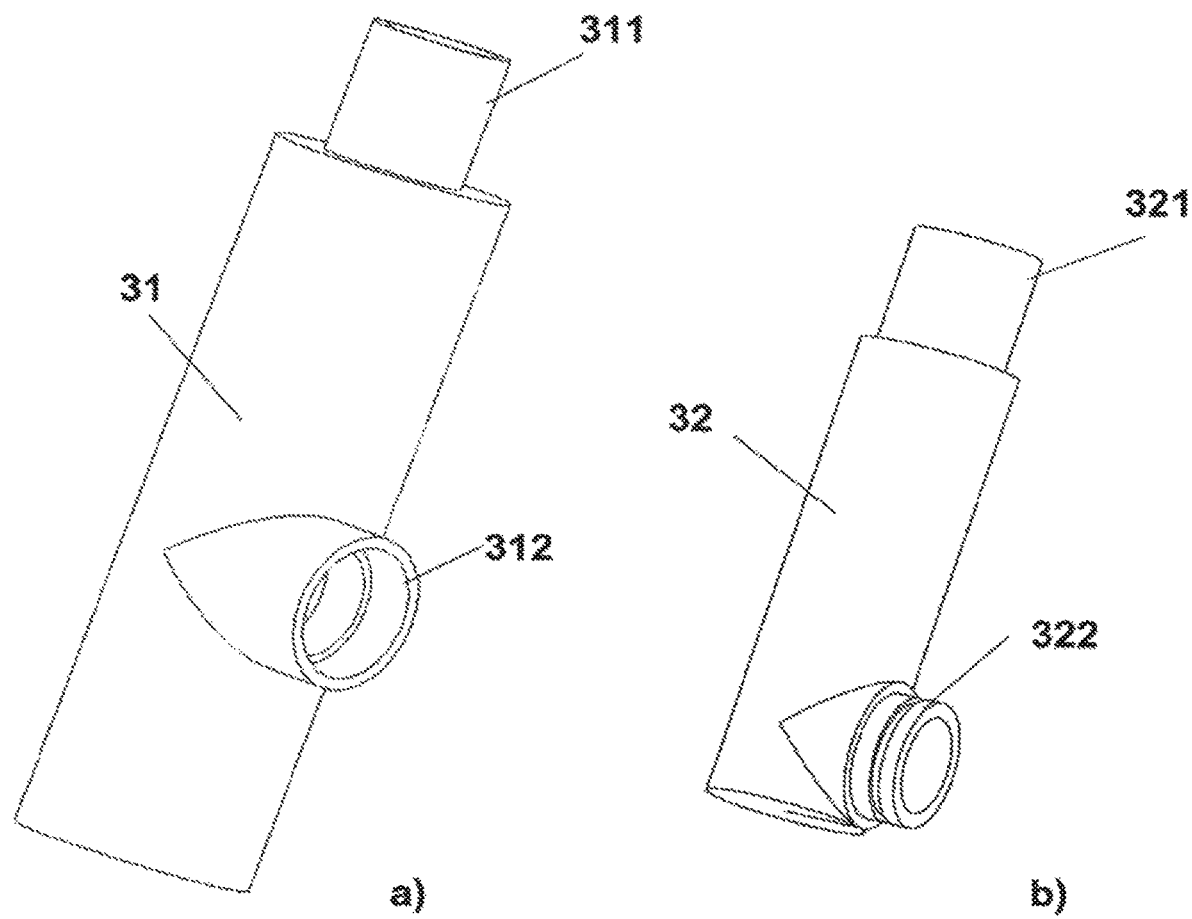
FIGS. 5a and b show an illustration of a pump module.

Laterally next to the first fluid channel 6', the intracardiac module 1 provides the fluid channel opening 61 of the second fluid channel 6, which opens out within the heart chamber. The two fluid channels 6 and 6' extend through the intracardiac module 1 separately and open out into the region of the extracardiac section 13a at the extracardiac fluid channel openings 54 and 62 that can be seen in FIG. 2b. The extracardiac fluid channel openings 54 and 62 each have a stepped plug-in contour 53', 63' of coaxial design, which, in the manner of a socket function, enables a fluid-tight insertion in each case of a pipe stub designed with a matching contour, to which reference is made in conjunction with the description of the pump module illustrated in FIGS. 5a and b.

The intracardiac module 1 has, in the region of the so-called medial section 12a, a cylindrically shaped outer contour, which serves as the joining contour 7 of the intracardiac module 1. The cylindrically shaped joining contour 7 is designed with a precise fit and a contour matching the joining contour 8 of the fastening module 2 illustrated in FIG. 3. The fastening module 2 preferably has an annular, plug-type spatial form with a tubus-form section 9, which on the radially inner side at least partially surrounds the joining contour 8, and onto which a collar 10 projecting radially beyond the tubus-form section 9 connects on one side. The straight cylindrically shaped joining contour 8 preferably extends over the entire axial length of the fastening module 2, and thus in the joined state fits in a fluid-tight manner over its entire axial length onto the joining contour 7 of the intracardiac module 1.

For purposes of a gentle insertion or feed of the tubus section 9 through a lesion which is a hole within the myocardium, the tubus-form section 9 tapers conically into an end region 9' facing away from the collar 10.

Furthermore, the collar 10 has one end face 11 facing away from the tubus section 9, and another end face 17 facing towards the tubus section 9.

The end face 11 is designed as an annular disk and is shaped and sized to a supporting surface 12 provided on the extracardiac section 13a of the intracardiac module 1. See FIG. 2a, on which in the joined state the end face 11 of the fastening module 2 fits flush between the intracardiac module 1 and the fastening module 2; with respect see in particular the overall illustration in FIG. 1.

For purposes of a mutually secure attachment in a releasable manner between the fastening module 2 and the intracardiac module 1, the fastening module 2 provides, in the region of the radially projecting collar 10, recesses 13 with internal threads, which are preferably designed as blind holes or holes projecting completely through the collar 10. With the aid of suitable screws 14, see FIG. 1, which can be inserted by way of the extracardiac section 13a of the intracardiac module 1 through correspondingly provided openings 15, these engage with the respective internal threads of the recesses 13.

For purposes of securing the fastening module 2 to the myocardium, the fastening module 2 has fastening structures 16, which are preferably mounted on the annular end face 17 facing towards the tubus section 9. The fastening structures 16 are preferably designed as surface elements which at least partially project radially beyond the collar 10 and can be pierced with a surgical needle, to be fixed in this way by a surgical thread to the surrounding myocardium. The fastening structures are formed, for example, from an artificial fabric material or a non-woven fabric, which can be brought into direct contact with the epicardium.

The pump module 3 illustrated in FIG. 1 has a U-shaped pipe system, along which a motor-driven fluid pump (not shown) is introduced. The U-shaped piping system of the pump module has two open-ended pipe stubs, which are arranged and designed such that they can be joined in a fluid-tight manner simply by axial insertion into the stepped plug-in contours 53' and 63' of the extracardiac fluid channel openings 54 and 62.

The U-shaped piping system of the pump module 3 is advantageously designed in two parts and has two separable pipe sections 31 and 32, which are illustrated both in the overall view of FIG. 1 and also in FIGS. 5a and b. In the pipe section 31, which opens out on the end face above and has a plug-in contour 311 of stepped design, which for purposes of fluid-tight joining can be connected into the matching plug-in contour 63' of stepped design, a motor-driven fluid pump (not shown) is integrated, which sucks in blood through the open top end of the pipe section 31. The pipe section 31 also has a pipe stub 312 transversely oriented to the longitudinal axis of the pipe section 31, which provides a fluid-tight connecting structure to a pipe stub 322 correspondingly provided on the second pipe section 32. The two pipe sections 31 and 32 are preferably connected to one another in a fluid-tight manner via their pipe stubs 312 and 322 in the manner of a plug-in connection using an O-ring seal. The second pipe section 32 also has at its upper end a plug-in contour 321 of stepped design, which correspondingly is designed with a contour matching the stepped plug-in contour 53 of the extracardiac fluid channel opening 54 of the first fluid channel 6'.

The pump module 3 described above is thus able to convey blood via the second fluid channel 6 from the heart chamber through the U-shaped piping system of the pump module 3 in the direction of the first fluid channel 5, which conveys the blood via the tubular extension 52, whose distal tube end 51 is located in the region of the aorta or is connected to an extension tube.

Figure 4:
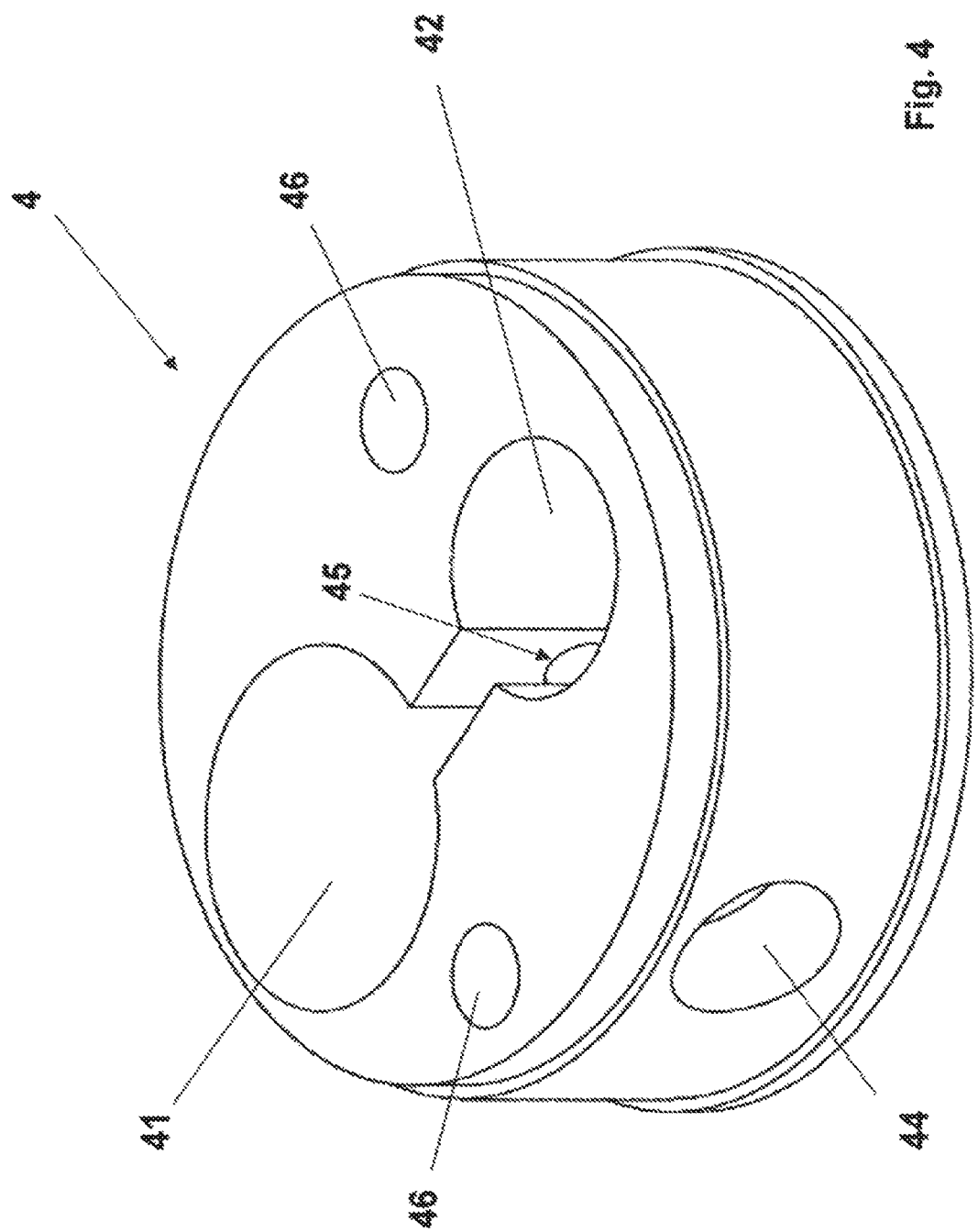
FIG. 4 shows an illustration of a first retaining module.

To ensure a secure connection of the pump module 3 to the corresponding extracardiac fluid channel openings 54 and 62 that can withstand mechanical loads, a retaining module 4 is provided, which is illustrated in FIG. 4. The retaining module 4 serves to provide an interdependent fastening of the two pipe sections 31 and 32. For this purpose, the essentially disk-shaped retaining module 4 provides two passageways 41 and 42, which pass completely through the retaining module 4 and whose inner diameters are respectively matched to the outer diameters of the pipe sections 31 and 32. From FIG. 4 it can be seen that the pipe section 31 surrounding the fluid pump, which is pushed through the passageway 41, possesses a larger diameter than the pipe section 32. For purposes of assembly the two pipe sections 31 and 32 are simply pushed through the corresponding passageways 41 and 42. With the aid of a fixing screw 43, in FIG. 1, which can be inserted through a screw opening 44 introduced laterally in the retaining module 4 and can be brought into engagement with an internal thread 45 provided within the retaining module 4, both pipe sections 31 and 32 are securely joined together by way of a form fit joint that is acted upon by a clamping force. The retaining module 4 also has further fastening openings 46, into which fastening screws 47 shown in FIG. 1 that can be inserted for purposes of a secure attachment in a releasable manner of the retaining module 4 relative to the intracardiac module 1.

In a preferred embodiment, the pipe section 31 is in its entirety a motor-driven diagonal pump that has already been certified and approved for medical use.

Figure 6:
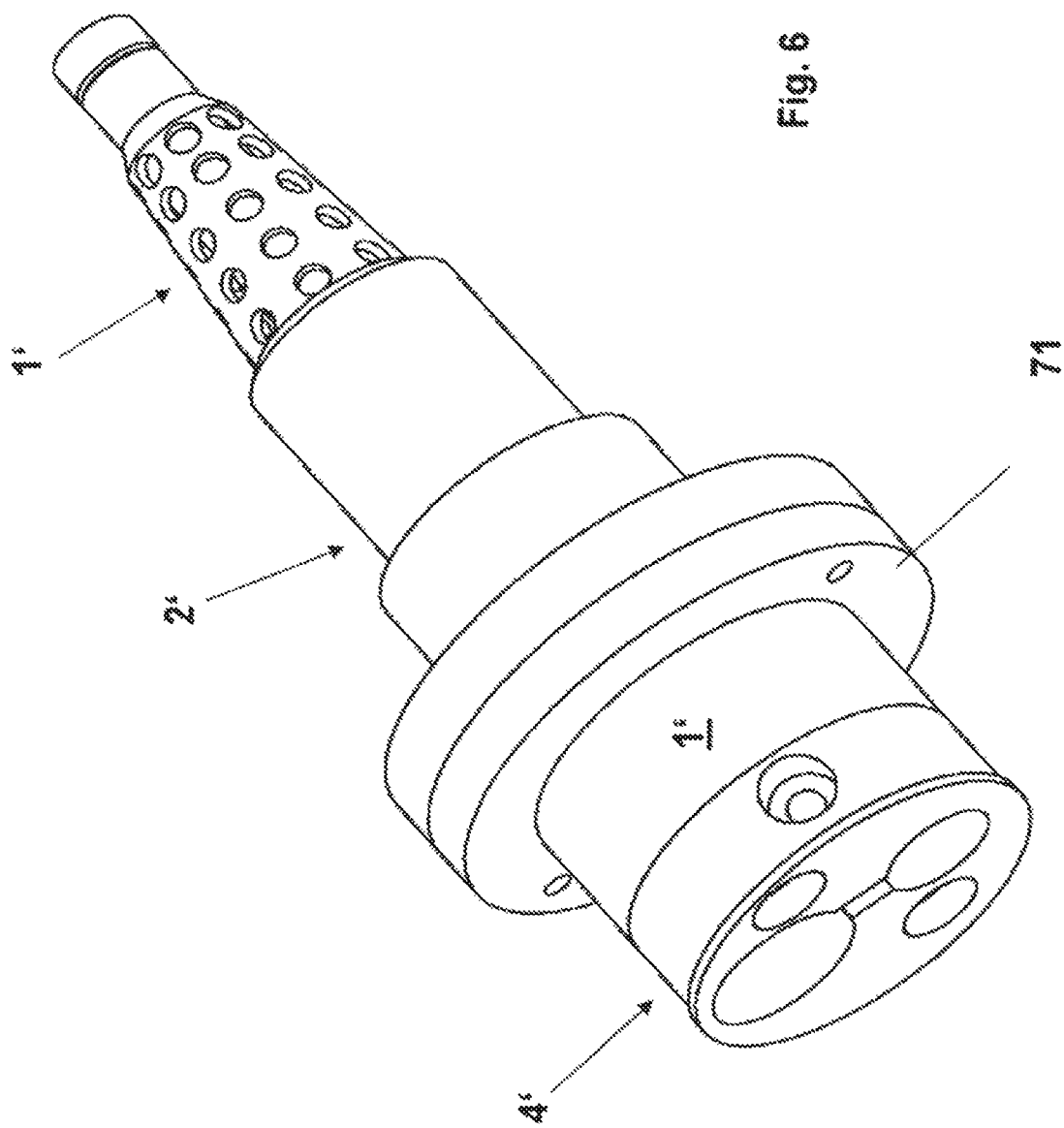
FIG. 6 shows a schematized illustration of a second implantable fluid pumping system without an illustration of the pump module.

FIG. 6 shows a schematic view in perspective of a second embodiment of an implantable fluid pumping system, which has the same modular construction as the embodiment illustrated in FIG. 1. It has an intracardiac module 1', a fastening module 2', a retaining module 4' and a pump module. The latter is not shown in the interest of more clarity. By virtue of the identical design of the retaining module 4' on the extracardiac side when compared with the retaining module 4, which is explained in more detail in FIG. 4, the pump module 3 can be adapted to the second embodiment in an unaltered design, for which reason any repetition of the illustration and explanation of the pump module 3 becomes unnecessary.

Figure 7:
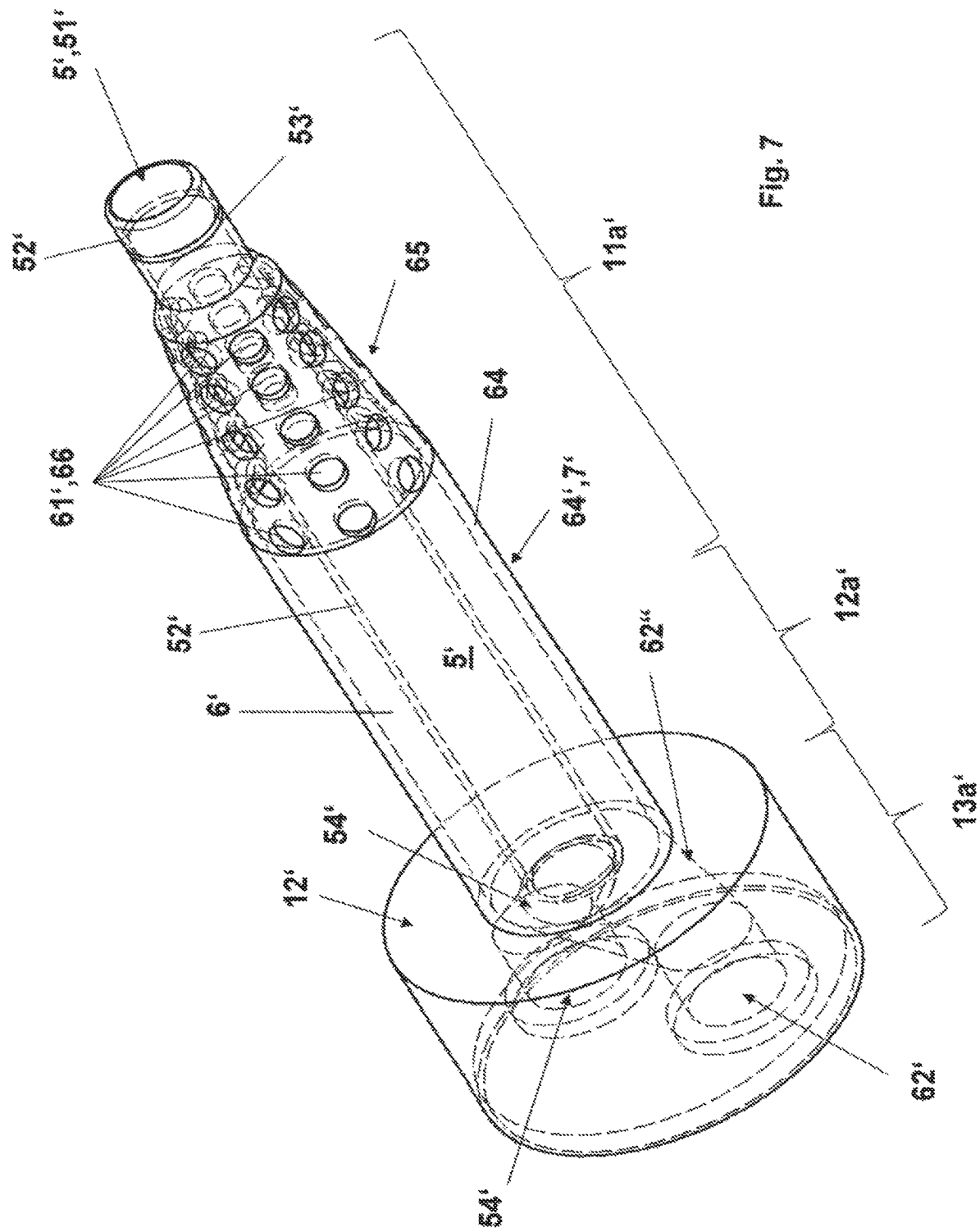
FIG. 7 shows in perspective a second intracardiac module.

In contrast to the first fluid pumping system shown in FIG. 1, the second embodiment has a modified construction with regard to the intracardiac module 1', which is shown on its own in FIG. 7.

The intracardiac module 1' is characterised by a substantially axisymmetric outer spatial form, which facilitates ease of implantation. The more so as the potential for observing the intracardiac location alignment of the intracardiac module 1 in the case of the first embodiment, by virtue of the lateral mounting of the second fluid channel 6 relative to the first fluid channel 6' in the first embodiment, now disappears as a result of the coaxial mounting of the first fluid channel 6' and the second fluid channel 6 in the second embodiment.

As with the intracardiac module 1 in FIG. 2, the intracardiac module 1' of FIG. 7 also has an intracardiac section 11a', a medial section 12a' and an extracardiac section 13a'.

The intracardiac module 1' comprises two fluid channels 6 and 6', each having open intracardiac fluid channel openings 51' and 61'. The first fluid channel 6' has a tubular extension 52', whose length is selected as a function of anatomical proportions. In a preferred embodiment, the tubular extension 52' has a length that is chosen so that in the implanted state the fluid channel opening 51' opens out into the region of the aorta. Alternatively it is possible to select the length of the tubular extension 52' to be appropriately short. By way of a fluid-tight connecting structure 53', which is provided in the region of the fluid channel opening 51', an artificial connecting tube, which is not shown in FIG. 7, can be securely mounted in a fluid-tight and releasable manner onto the tubular extension 52' so as to guarantee a direct supply of blood to the aorta. The formation of the connecting structure 53' is particularly advantageous in those cases in which the artificial connecting tube is preferably fixed in the region of the heart valves, for example with the aid of a dilatation element.

An outer pipe 64 is arranged radially around the tubular extension 52'. The axial extent of the outer pipe is dimensioned to be smaller than the tubular extension 52', and with the tubular extension 52' encloses a gap in the form of an annular channel, which is assigned to the second fluid channel 6. The outer pipe 64 has a straight cylindrically shaped outer surface 64', which serves as a joining contour 7' of the intracardiac module 1'.

The cylindrically shaped joining contour 7' is designed with a precise fit and a contour matching the joining contour 8' of the fastening module 2' shown in FIG. 8, which will be discussed further below.

The outer pipe 64 terminates on one side on a supporting surface 12' that is radially wider relative to the outer pipe, and which corresponds to a boundary surface of the extracardiac section 13a' of the intracardiac module 1. The first and second fluid channels 6' and 6 open out within the extracardiac section 13a' via their respective extracardiac fluid channel openings 54' and 62'. For this purpose, the central fluid channel 5' is connected to the extracardiac fluid channel opening 54' via a lateral outlet 54''. A second lateral outlet 62'' connects the annular fluid channel 6' to the extracardiac fluid channel opening 62' without penetrating the lateral outlet 54''.

On the intracardiac side, a conical transition sleeve 65 is positioned flush onto the outer pipe 64. The outer diameter of the sleeve decreases with increasing axial distance from the outer pipe 64 down to the dimension of the outer diameter of the tubular extension 52'. In the same way as the outer pipe 64, the transition sleeve 65 encloses a gap with the tubular extension 52', which is part of the second fluid channel 6. The sleeve wall of the transition sleeve 65 has a multiplicity of passageways 66, via which access to the second fluid channel 6 is created. The entirety of all passageways 66 represents the intracardiac fluid channel opening 61' to the second fluid channel 6.

The fastening module 2' serves to provide the fastening of the intracardiac module 1' onto the heart. The fastening module is shown in FIG. 9 and preferably has an annular, plug-type spatial form with a tubus section 9''', which on the inner side radially surrounds the joining contour 8', and onto which a collar 10' projecting radially beyond the tubus section 9''' connects on one side. The straight cylindrically shaped joining contour 8' preferably extends over the entire axial length of the fastening module 2' and thus in the joined state fits in a fluid-tight manner over its entire axial length onto the join contour 7' of the intracardiac module 1'.

For purposes of gentle insertion or feeding of the tubus section 9''' through a lesion in the form of a hole within the myocardium, the tubus section 9''' tapers conically into an end region 9''' facing away from the collar 10'.

Furthermore, the collar 10' has one end face 11' facing away from the tubus section 9''' and another end face 17' facing towards the tubus section 9'''.

The end face 11' is an annular disk and, in the joined state, fits directly or indirectly with the intracardiac module 1' on the supporting surface 12' provided on the extracardiac section 13a' of the intracardiac module 1'. In the overall view in FIG. 7, an intermediate ring 71 is additionally introduced between the supporting surface 12' and the fastening module 2'.

Both for purposes of a releasability and secure assembly of the intracardiac module 1' with the fastening module 2' in a releasable manner, and also for purposes of the mounting of the fastening module 2' onto the myocardium, the same precautions are taken as in the embodiment of FIG. 1. Thus fastening structures 16 are mounted peripherally around the supporting surface 17' of the fastening module 2' which are surface elements at least partially projecting radially from the collar 10', which can be pierced by a surgical needle to be fixed in surgical thread to the surrounding myocardium. The fastening structures 16' are formed, for example, from an artificial fabric material or a non-woven fabric, which can be brought into direct contact with the epicardium.

Furthermore, the retaining module 4' adjoins the intracardiac module 1' on the extracardiac side in the same way as in the case of the preceding embodiment. By virtue of its identical design, the retaining module 4' allows mounting of the pump module 3 in the same way as has already been explained in FIG. 5.

Figure 8:
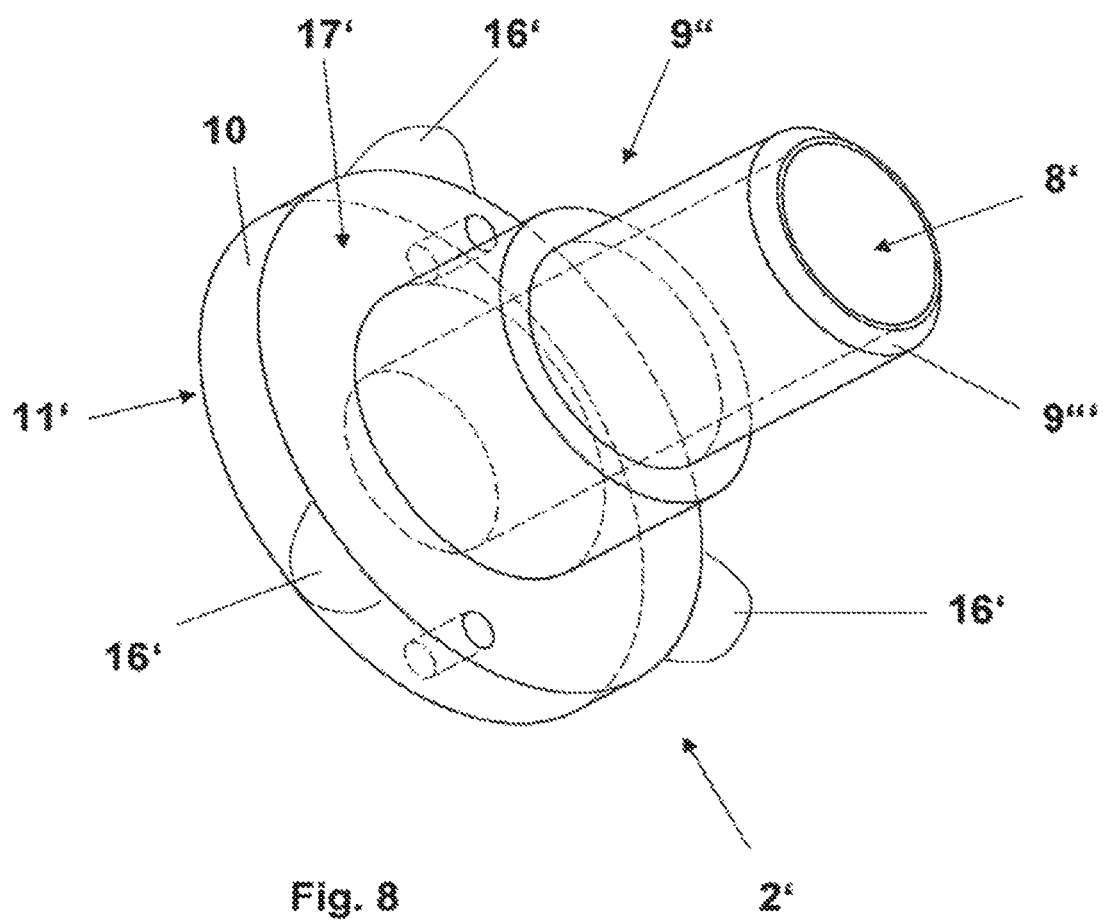
FIG. 8 shows a of a second fastening module.
Figure 9A:
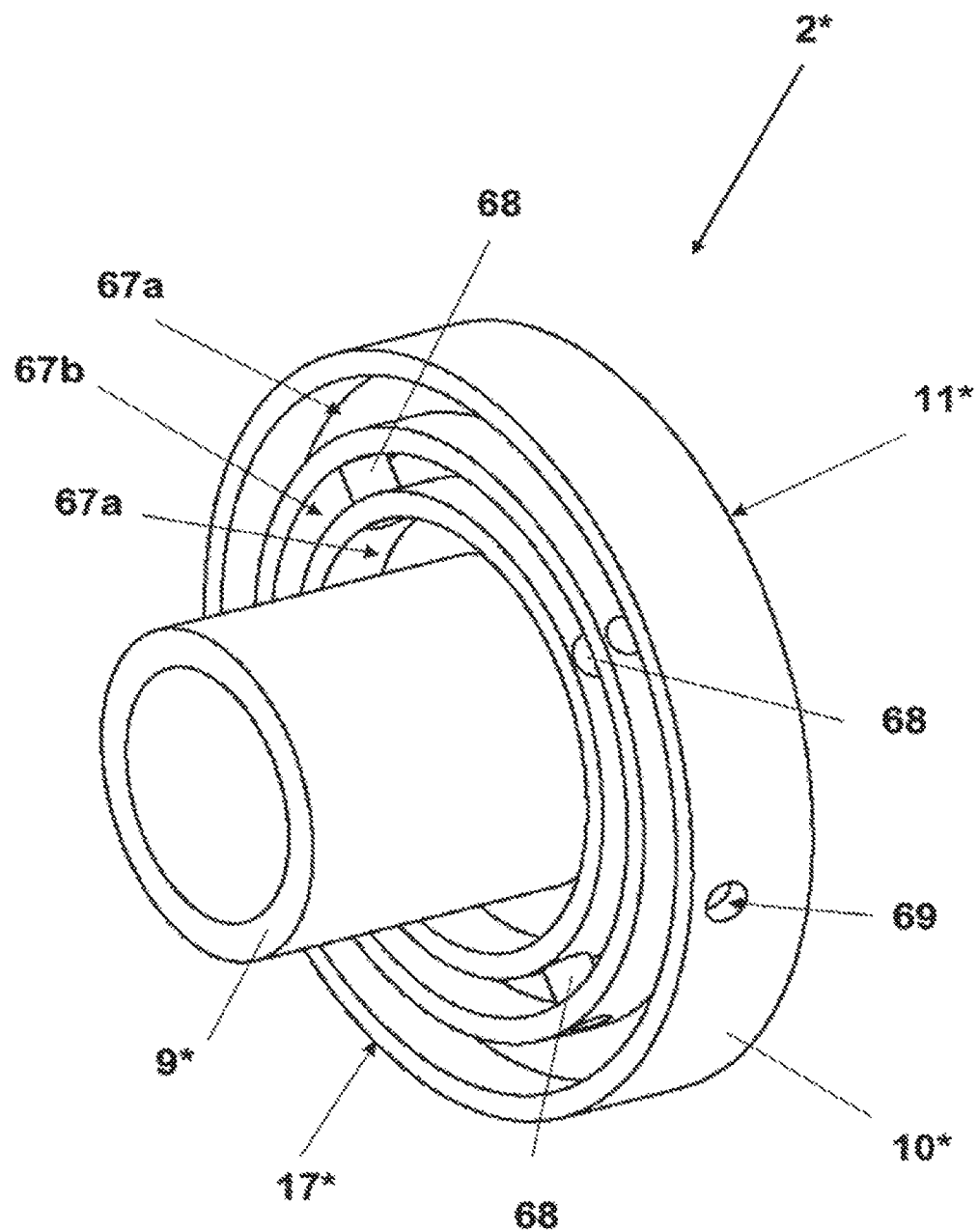
FIGS. 9a, b and c show illustrations of a modification concerning the fastening module.
Figure 9B:
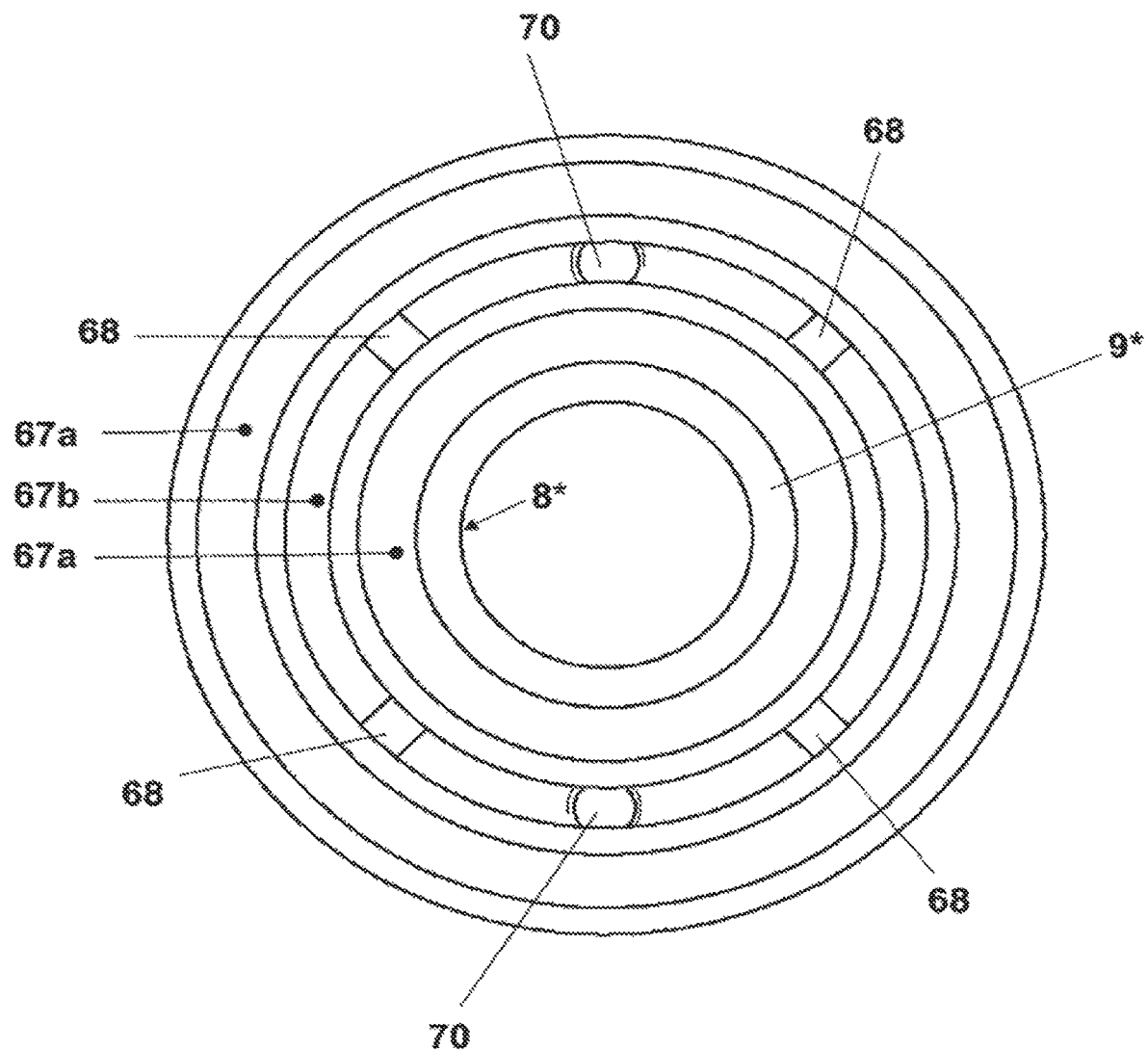
Figure 9C:
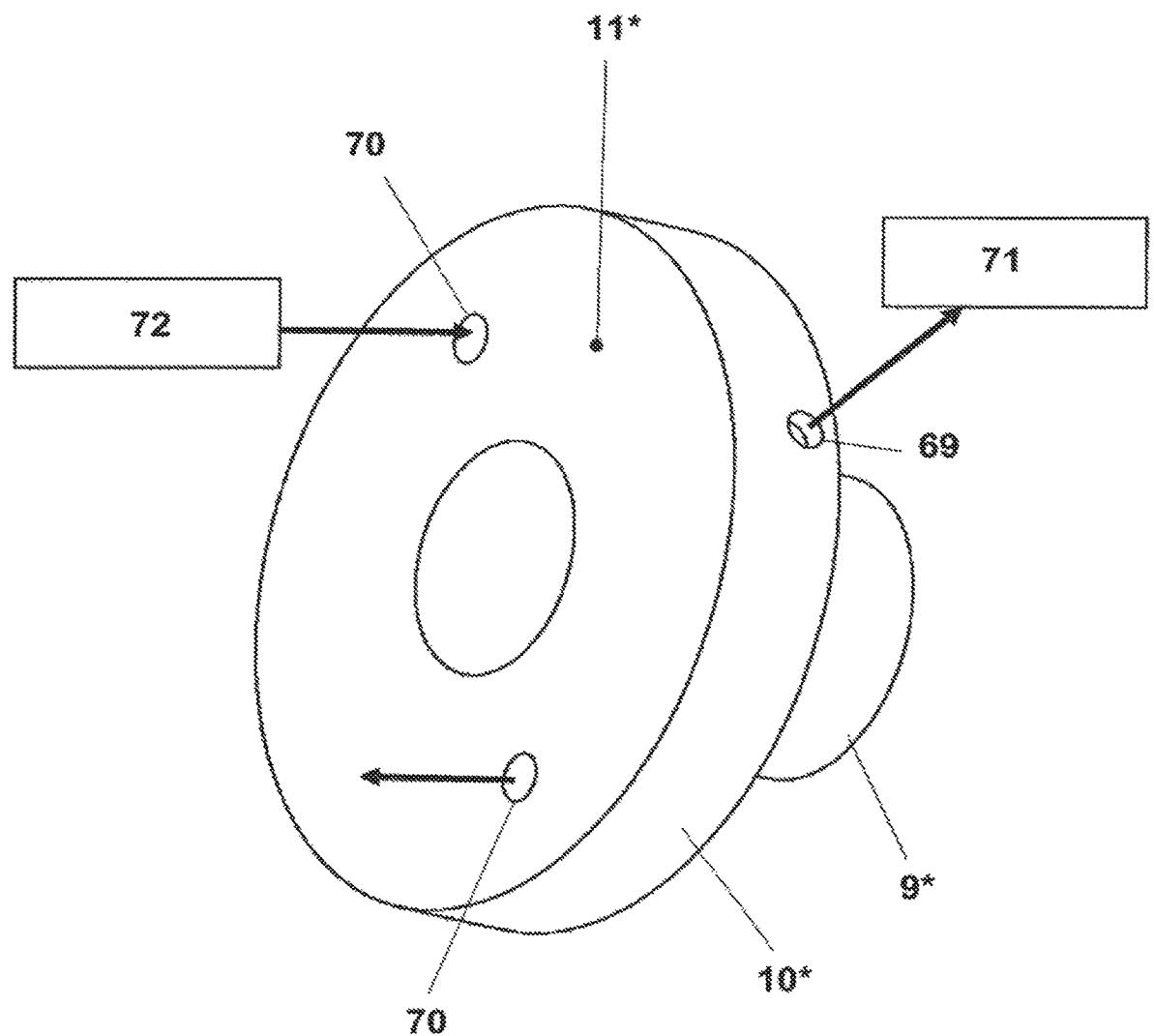

FIGS. 9a, b and c illustrate a fastening module 9\* that possesses a modified collar 10\*, which has an alternative or an additional attachment mechanism to the fastening structures 16 already described. For purposes of a clearer illustration and explanation of the collar modification, FIG. 9a shows an illustration in perspective with a view onto the end face 17\* of the collar 10\*, wherein the tubus-form section 9\* can be of the same design as section 9 of the embodiment in FIG. 3, and section 9''' of the embodiment in FIG. 8. FIG. 9b shows an axial view onto the collar 10\*. FIG. 9c shows a rear view of the collar 10\* onto the end face 11\*. The further description makes reference to all three images in FIGS. 9a to c.

The modified collar 10\* has groove-shaped recesses 67a and 67b that open out onto the end face 17\*, which is comparable with the end face 17 or 17', and which in each case is oriented towards the myocardium. The groove-shaped recesses 67a and 67b, in the embodiment illustrated are in each case designed as circular grooves, preferably with rectangular cross-sections, arranged concentrically around the join contour 8\*. The radially outer recess 67a and the radially inner recess 67a are connected to one another in terms of fluid flow via connecting channels 68. For this purpose, the connecting channels 68 are in each case designed in the form of connecting sleeves, and pass through the groove-shaped recess 67*b* arranged radially between the groove-shaped recesses 67*a* in a fluid-tight manner. In the embodiment illustrated, four connecting channels 68 are provided which are arranged in the circumferential direction of the circular recesses 67*a* and 67*b* in a uniformly distributed manner. Through the peripheral circumferential edge of the collar 10*, an access opening 69 is introduced to the lumen of the radially outer recess 67*a* which is preferably a fluid-tight connection to a reduced pressure source, which applies reduced pressure within the radially outer and inner recesses 67*a*. Also possible is a connection to a media source for purposes of supplying the radially outer and inner recesses 67*a* with a medium, for example a biocompatible adhesive.

Furthermore, two passageways 70 are introduced through the rear end face 11* of the modified collar 10* which provide access of fluid flow to the centrally arranged recess 67*b*. It should be noted that the radially centrally arranged connecting channels 68, which locally traverse across the groove-shaped recess 67*b*, possess a smaller outer diameter than the depth of the groove-shaped recess 67*b*. In this way, when a medium is being fed into the lumen of the radially centrally arranged recess 67*b*, it can be distributed evenly and can completely fill the lumen. For purposes of feeding or filling the lumen, a medium is fed through one of the two passageways. If the medium that is being fed in exits through the other passageway, the lumen is completely filled.

The term "lumen", which was also used above in connection with the recesses 67*a*, is understood to mean the volume enclosed in each case by a circular, groove-shaped recess 67*a* and 67*b*, which in each case is bounded in the direction of the one side that is open by the abutment of the end face 17* of the collar 10* onto a boundary surface, for example in the form of the myocardial outer wall.

The modification of the collar 10* allows a possible alternative method of fixing the fastening module 2* onto the myocardial wall, which after positioning of the fastening module on the myocardium, a reduced pressure or suction is temporarily applied by a reduced pressure source 71 shown in FIG. 9*c*, via the passageway 69 along the radially inner and outer recesses 66*a*. By this, the whole of the end face 17* is sucked onto the myocardial wall, as a result of which the central recess 67*b* in particular encloses a fluid-tight lumen by the suction-conditioned pressure of the groove walls, bounding the central groove-shaped recess on both sides, onto the myocardial wall in a fluid-tight manner. If the surgeon should detect a malpositioning of the fastening module, readjustments can be made by briefly relieving the reduced pressure so as to allow a repositioning of the fastening module on the myocardium. Optionally, the collar 10* has fastening structures 16* mounted onto the peripheral edge, Compare the above description which relates to FIGS. 3 and 8.

Subsequently, an injection of adhesive takes place through one of the two passageways 70 into the lumen of the central, groove-shaped recess 67*b*, by a media source 72, which is suitable for the metered delivery of biocompatible adhesive, as shown in FIG. 9*c*. The biocompatible adhesive spreads evenly within the groove-shaped recess 67*b* and forms an annular adhesive surface, which encloses in an airtight manner the lesion in the form of a hole within the myocardial wall, through which the fastening module projects. A complete filling of the lumen with adhesive is achieved when the adhesive emerges from the opposite passageway 70 along the groove-shaped recess 67*b* for adhesive injection.

The embodiment described above thus not only simplifies the fastening of the fastening module to the myocardial wall, but also ensures that this is securely airtight relative to the outer environment. In this way, air embolisms can be excluded.

The modularity of the invention is implantable fluid pumping system not only enables the separate replacement of individual components, but also offers the possibility of an individual assembly of the individual components in shape and size to meet the individual patient's anatomical requirements and proportions. Thus, individual components that are different in shape and size, but matched to one another, can be stored as a modular range, to offer the surgeon in question individual options when deciding on the assembly of the implanted fluid pump system.

The shape and size of the individual components, together with, for example, the relative arrangement of the first and second fluid channels 6' and 6 in the intracardiac module 1, 1' can be designed such that they deviate from the specific embodiments that are illustrated. It is essential that a pump-driven blood flow can be managed from the heart chamber via the pump module and directly or indirectly via the tubus-form extension into the aorta. At the same time, it is also possible to implant the implantable fluid pump system into the right ventricle, wherein in this case the open tube end 51 and 51', or a further hollow channel connected to the open tube end 51 and 51', is positioned in the pulmonary artery.

Figure 3:
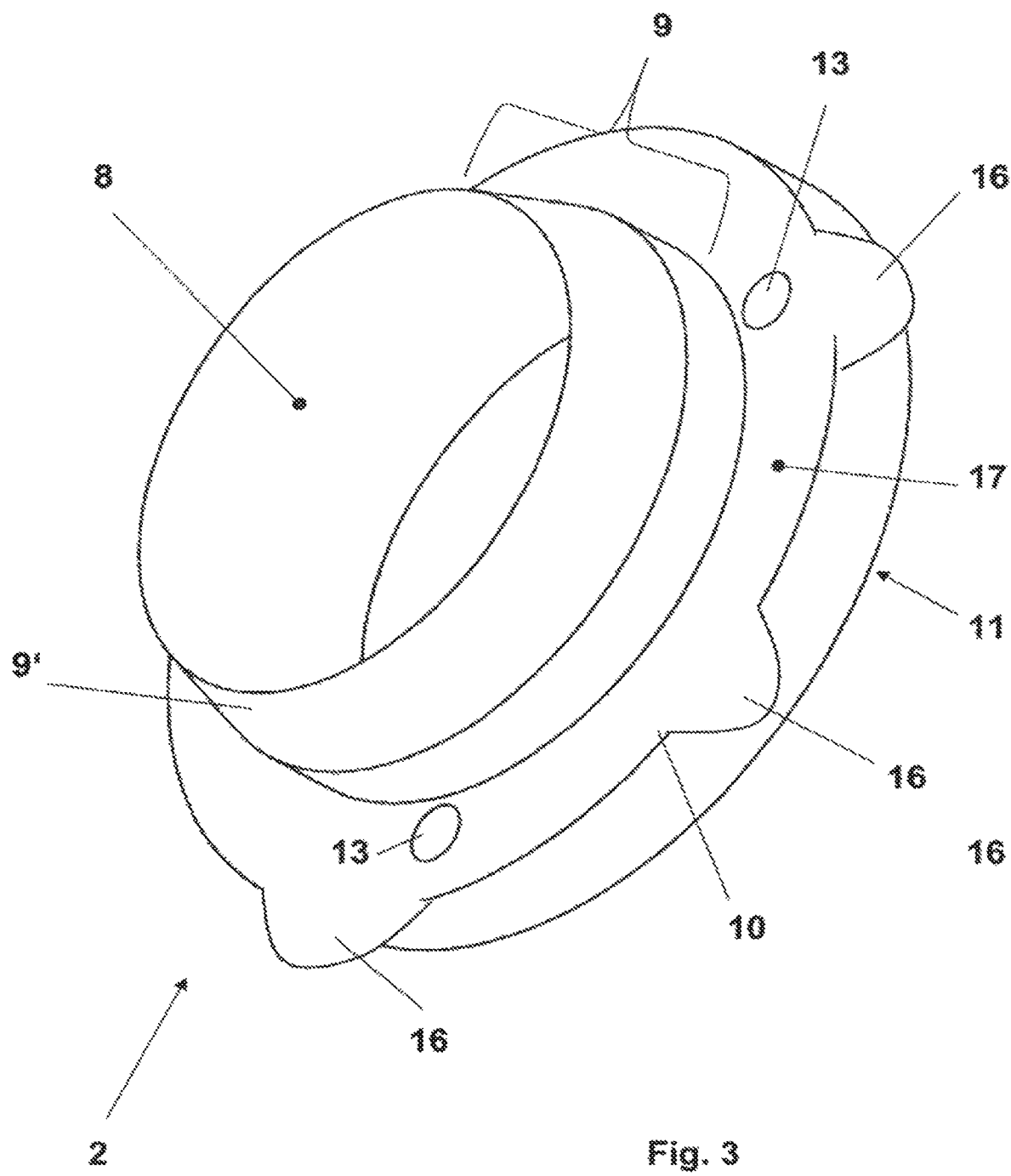
FIG. 3 shows an illustration of a first fastening module.

The fluid pumping system of the invention makes it possible to use a minimally invasive surgical technique in which, after an apical puncture of the myocardium, a Seldinger wire S is placed intracardially in the aorta. With the aid of a trocar T illustrated in FIG. 10, on the shoulder T1 of which the fastening module 2 of the above-described first embodiment in FIGS. 1 to 3 is positioned, the conically-tapering trocar tip T2 is placed apically on the myocardium with the aid of the Seldinger wire S. By carefully advancing the trocar tip T2 into the myocardium, the latter is laterally expanded radially until the myocardium fits against the radial outer side of the tubus section 9. A surgical fastening of the fastening module 2 onto the myocardium then takes place. The trocar T is removed on the proximal side and replaced by the intracardiac module, on which the pump module has already been mounted with the aid of the retaining module.

In the case of the above-described second embodiment in FIGS. 6 to 8, a trocar T for introducing the retaining module 2' through the myocardial wall is not absolutely necessary. This is especially so since as a result of the slim design of the intracardiac module 1' the retaining module 2' and the intracardiac module 1' can be implanted together. Therefore, the intracardiac module 1' is in the retaining module 2'. Care must be taken that the intracardiac fluid channel openings 51' and 61' are closed during the implantation. A closure of these fluid channel openings 51' and 61' can be implemented by suitable covering surfaces, which by rotation of the intracardiac module 1' within the retaining module 2', largely cover the respective fluid channel openings in a fluid-tight manner.

The secure connection between the intracardiac module and the fastening module fastened to the myocardium takes place with the aid of the screwed joints explained above. Should subsequent servicing or replacement measures be required, in particular a replacement of the pump module, there need be no irritation of the myocardium, especially since the pump module is arranged extracardially and accordingly can be replaced in a minimally invasive manner.

REFERENCE LIST 1, 1' Intracardiac module
11a and 11a' Intracardiac section
12a and 12a' Medial section
13a and 13a Extracardiac section
2, 2' Fastening module
3 Pump module
4, 4' Retaining module
5 Dot dash line
6' First fluid channel
6 Second fluid channel
7, 7' Joining contour
8, 8' Joining contour
9, 9" and 9* Tubus-form section
9' Conical section
9''' Conical section
10, 10' Collar
11, 11' End face
12, 12' Supporting surface
13 Recess
14 Screw
15 Screw opening
16 Fastening structure
17, 17' End face
31 Pipe section
311 Plug-in structure
312 Stub
32 Pipe section
321 Plug-in structure
322 Connecting stub pipe
41 Passageway
42 Passageway
43 Fastening screw
44 Screw opening
45 Internal thread
46 Fastening opening
47 Fastening screw
51 and 51' Intracardiac fluid channel opening
52 and 52' Tubular extension
53 Connecting structure
53' Stepped Contour
54 and 54' Extracardiac fluid channel opening
55 Stepped plug-in contour
61 and 61' Intracardiac fluid channel opening
62 and 62' Extracardiac fluid channel opening
63 Connecting structure
63' Stepped Contour
64 External pipe
65 Transition sleeve
66 Passageway
67a Groove-shaped recess
67b Groove-shaped recess
68 Connecting channel
69 Passageway
70 Passageway
71 Reduced pressure source
72 Media source
T Trocar
T1 Trocar shoulder
T2 Trocar tip
S Seldinger wire

The invention claimed is:

1. An implantable fluid pumping system configured for supporting or initiating blood flow inside a heart which is modular in construction, includes an intracardiac module, a fastening module, a pump module and a retaining module and the modules are configured to be assembled, implanted and connected to the heart comprising:

the intracardiac module including an intracardiac section to be positioned inside the heart and an extracardiac section to be positioned outside the heart, at least two separated fluid channels with each separated fluid channel including at least one intracardiac fluid channel opening and at least one extracardiac fluid channel opening opposing the at least one intracardiac fluid channel opening and when implanted including at least the intracardiac section with one of the intracardiac channels opening into the one chamber of the heart and another one of the intracardiac fluid channels protruding into the aorta or the pulmonary artery and the extracardiac section;

the fastening module including a joining contour to provide an intracorporeal fluid tight connection to a matching contour of the intracardiac module when implanted and a fastening structure for intracorporeal fastening to an opening in the myocardium of the heart; and the pump module being configured to be releasably fixed to the retaining module to permit replacement without irritation of the myocardium and which is attached to the extracardiac section of the intracardiac module and which is releasably attached to the pump module when the system is implanted, the retaining module comprising two openings that completely pass through the retaining module that engage the at least two separated fluid channels of the intracardiac module and the pump module being releasably attached to the openings of the retaining module and fixed to the extracardiac section in a fluid tight manner; and wherein the retaining module is positioned when implanted between the pump module and the intracardiac module.

2. The implantable fluid pumping system in accordance with claim 1, wherein the intracardiac module, when implanted in an axial direction between the intracardiac section and the extracardiac section, has a medial section, the intracardiac section including a tubular extension with an open distal tube end surrounding one of the two fluid channels, and positioned laterally spaced from, or is radially positioned around the tubular extension and the at least one intracardiac fluid channel opening of the other fluid channel, the medial section including a peripherally surrounding joining contour which matches the joining contour of the fastening module, and open fluid channel openings of both fluid channels open into the extracardiac section.

3. The implantable fluid pumping system in accordance with claim 2, wherein the joining contour peripherally surrounding the medial section of the intracardiac module is shaped as one of a straight cylinder, a cone or a prism; and the fastening module includes a ring with a radially inner opening which peripherally is surrounded by the joining contour of the fastening module.

4. The implantable fluid pumping system in accordance with claim 1, wherein the fastening module comprises a plug having a tubus section, which on an inner side at least partially surrounds the joining contour of the fastening module, and on which a collar is connected and which projects on one side thereof radially beyond the tubus section.

5. The implantable fluid pumping system in accordance with claim 2, wherein the fastening module comprises a plug having a tubus section, which on an inner side at least partially surrounds the joining contour of the fastening module, and on which a collar is connected and which projects on one side thereof radially beyond the tubus section.

6. The implantable fluid pumping system in accordance with claim 3, wherein the fastening module comprises a plug having a tubus section, which on an inner side at least partially surrounds the joining contour of the fastening module, and on which a collar is connected and which projects on one side thereof radially beyond the tubus section.

7. The implantable fluid pumping system in accordance with claim 4, wherein the collar has an end face facing from the tubus section, which is complimentary in shape and size to a supporting surface provided on the extracardiac section of the intracardiac module, on which when joined to the end face of the fastening module fits between the intracardiac module and the fastening module.

8. The implantable fluid pumping system in accordance with claim 1, wherein the pump module comprises a U-shaped pipe system, including a motor-driven fluid feed pump having two pipe stubs with open ends which are configured to be connected to be fluid-tight and is releasable from a fluid-tight plug-in connection to the at least one extracardiac fluid channel opening of the fluid channels.

9. The implantable fluid pumping system in accordance with claim 8, wherein the U-shaped piping system has two separable pipe sections and the motor-driven pump is integrated along one of the two separable pipe sections.

10. The implantable fluid pumping system in accordance with claim 8, wherein an open-ended pipe stub of one of the two pipe stubs is connectable to be fluid-tight and releasable from an end of the extracardiac fluid channel.

11. The implantable fluid pumping system in accordance with claim 9, wherein the motor-driven fluid feed pump is a diagonal pump on which another pipe section is connected laterally which is fluid-tight.

12. The implantable fluid pumping system in accordance with claim 4, wherein the collar includes an annular end face facing toward the tubus section, on which is fastened a surface element at least partially projecting radially beyond the annular end face and which is pierceable with a surgical needle to be configured for attaching the implantable fluid pumping system with thread to the heart.

13. The implantable fluid pumping system in accordance with claim 2, comprises a region of a distal tube end of the tubular extension, a connecting structure is mounted with a fluid-tight fitting to a hollow channel section extending along the length of the tubular extension.

14. The implantable fluid pump system in accordance with claim 13, wherein the connecting structure comprises a plug-in or a screw thread contour.

15. The implantable fluid pumping system in accordance with claim 2, wherein the at least two separated fluid channels are relative to each other to be either laterally or coaxially within the intracardiac module.

16. The implantable fluid pumping system in accordance with claim 4, wherein the collar includes an annular end facing towards the tubus section, at least two separated recesses which open into the annular end face on one side, and the at least two separated recesses are separated by at least one passageway which penetrates the collar.

17. The implantable fluid pumping system in accordance with claim 16, comprising a fluid tight reduced pressure source connected by a passageway to at least one recess and a media source is connected by a fluid-tight connection by another passageway to at least one other recess.

18. The implantable fluid pumping system in accordance with claim 16, comprising:
- at least three grooved recesses, concentrically disposed relative to one another and which open out on one side onto the annular end face, at least one of the three recesses is surrounded by a radially outer recess and a radially inner recess, the at least one of the grooved recesses is connectable by at least one passageway which penetrates the collar connected to a media source or a reduced pressure source;
- radially outer and inner recesses communicate by fluid flow between each other by at least one connecting channel; and
- at least one of the radially outer and the radially inner recesses is connectable by at least one passageway which penetrates the collar and is which connected to a media source or a reduced pressure source.

* * * * *